United States Patent [19]

Gordon

[11] 4,440,723
[45] Apr. 3, 1984

[54] BLOOD OXYGENATOR

[75] Inventor: Lucas S. Gordon, Fountain Valley, Calif.

[73] Assignee: Bentley Laboratories, Inc., Irvine, Calif.

[21] Appl. No.: 282,283

[22] Filed: Jul. 10, 1981

[51] Int. Cl.³ .............................................. A61M 1/03
[52] U.S. Cl. ............................... 422/47; 128/DIG. 3; 422/46
[58] Field of Search .................................. 422/46, 47; 261/DIG. 28; 128/DIG. 3

[56] References Cited

U.S. PATENT DOCUMENTS

| | | |
|---|---|---|
| 3,204,631 | 9/1965 | Fields . |
| 3,468,631 | 9/1969 | Raible et al. . |
| 3,488,158 | 1/1970 | Bentley et al. . |
| 3,547,591 | 12/1970 | Torres ..................................... 422/47 |
| 3,578,411 | 5/1971 | Bentley et al. . |
| 3,615,238 | 10/1971 | Bentley . |
| 3,764,271 | 10/1973 | Brumfield et al. . |
| 3,768,977 | 10/1973 | Brumfield et al. ..................... 422/46 |
| 3,769,162 | 10/1973 | Brumfield et al. . |
| 4,058,369 | 11/1977 | Bentley . |
| 4,138,464 | 2/1979 | Lewin . |
| 4,158,693 | 6/1979 | Reed et al. .............................. 422/46 |
| 4,160,801 | 7/1979 | Badolato et al. ....................... 422/46 |
| 4,282,180 | 8/1981 | Raible ................................. 422/47 X |
| 4,297,318 | 10/1981 | Raible ................................. 422/47 X |

*Primary Examiner*—Barry S. Richman
*Attorney, Agent, or Firm*—Lyon & Lyon

[57] ABSTRACT

A blood oxygenator containing a means for combining oxygen-containing gas with liquid blood, the oxygenator having an outer shell portion rotatably joined to a cap portion. Preferably the cap portion includes at least one blood inlet together with an oxygen-containing gas inlet while the outer shell portion contains at least one oxygenated blood outlet and the rotatable joint between said outer shell portion and said cap portion is in venting communication with the exterior of the blood oxygenator.

5 Claims, 4 Drawing Figures

BLOOD OXYGENATOR

BACKGROUND OF THE INVENTION

The invention herein relates to a blood oxygenator having a cap portion which is rotatably joined to an outer shell portion.

The history of safe and relible blood oxygenators is relatively brief. Such oxygenators are used in open-heart surgery and other operations and treatments of the body when it is necessary to establish an extracorporeal circulation system for temporarily assuming the functions of the heart and lungs of the patient. In such a system, the oxygenator operates to perform the function usually performed by the lungs of the patient, i.e., the life-supporting transfer of oxygen into the blood and carbon dioxide out of the blood. The oxygenator is used in association with a pump which performs the function of the heart to cause circulation of the blood. Thus, early versions of the oxygenator were often referred to as "heart-lung" machines. The early heart-lung machines were typically rotating discs which passed through a pool of blood, but were only partially immersed therein such that the free surface of the disc exposed the blood to oxygen and accomplished some gas transfer. After this, bag-type oxygenators were introduced which were superior to the disc oxygenators, but which left much to be desired.

A major advance occurred in the mid-1960's when the rigid (or hard shell) bubble oxygenator was developed. The history of such oxygenators had its beginnings in the device shown in Raible, et al, U.S. Pat. No. 3,468,631, which is incorporated herein by reference, and they first came into clinical use with the development of the devices shown in Bentley et al, U.S. Pat. Nos. 3,488,158 and 3,578,411 which have come to be known as the Bentley Oxygenator. At the present time, such oxygenators are used more frequently than any other type. Among the important features of the oxygenators disclosed in the foregoing patents was the provision of a self-contained heat exchanger.

In the intervening years, some relatively minor modifications have been made in bubble oxygenators, e.g., those disclosed in Brumfield U.S. Pat. Nos. 3,764,271 and 3,769,162. However, all rigid bubble oxygenators shown in the aforesaid patents and all other such oxygenators known to applicant to have been put to actual clinical use have had one fundamental feature in common, namely, each of them introduced blood and oxygen-rich gas in the lower region of the device and caused a column of bubbles to flow upwardly through the initial portion of the device. Bentley, et al, U.S. Pat. Nos. 3,488,158 and 3,578,411 and the aforesaid Brumfield Patents do have some downward portions in the flow path of the gas blood mixture, but it is clear that they were designed to provide for initial upwardly flow of the gas and blood mixture in that portion of the flow path where the bubbles are formed. In addition, Fields U.S. Pat. No. 3,204,631, discloses an oxygenator in which blood enters at an upper portion and oxygen enters at a lower portion such that there is a counter-flow relationship with the blood initially flowing downwardly and the oxygen flowing upwardly. Further Lewin U.S. Pat. No. 4,138,464 shows the desirability of alternate positioning of fluid connections for an oxygenator device.

The present invention is a further improvement of the device shown in the Bentley U.S. Pat. No. 3,615,238, issued Oct. 26, 1971, entitled "Oxygenator"; the Bentley, et al, U.S. Pat. No. 3,578,411 issued May 11, 1971, entitled "Bubbler Assembly for Blood Treating Apparatus"; the Bentley, et al U.S. Pat. No. 3,488,158 issued Jan. 6, 1970, entitled "Bubbler Assembly for Oxygenator"; and application, Ser. No. 436,913, entitled "Blood Oxygenator", now abandoned, Ser. No. 565,043, now U.S. Pat. No. 4,058,369, entitled "An Improved Oxygenating Device", and Ser. No. 54,268 entitled "Blood Oxygenator" issued as U.S. Pat. No. 4,297,318 the disclosures of which are incorporated by reference herein. These devices each represent important developments in the blood treatment art. However, since these devices temporarily assume the function of the heart and lungs of a patient during certain operations or other treatments of the body, further improvements are desired.

SUMMARY OF THE INVENTION

The present invention is directed to a blood oxygenator which contains a means for combining oxygen-containing gas with liquid blood, the oxygenator having an outer shell portion which is rotatably joined to a cap portion. This ability to rotate the outer shell portion of the blood oxygenator with respect to the cap portion facilitates the safe operation of the device in that medical personnel may rotate the device in order to monitor fluid flow through selected connection points of the blood oxygenator. Further the ability to rotate the outer shell portion of the blood oxygenator with respect to the cap portion decreases the likelihood that flexible connections to the blood oxygenator will become partially occluded or kinked during setup or operation of the blood oxygenator.

In the preferred embodiment the cap portion of the blood oxygenator includes at least one blood inlet together with an oxygen-containing gas inlet, while the outer shell portion contains at least one oxygenator blood outlet. It is also preferred that the rotatable joint between the cap portion of the blood oxygenator and the outer shell portion be in venting communication with the exterior of the blood oxygenator.

DESCRIPTION OF PREFERRED EMBODIMENTS

Figure 1:
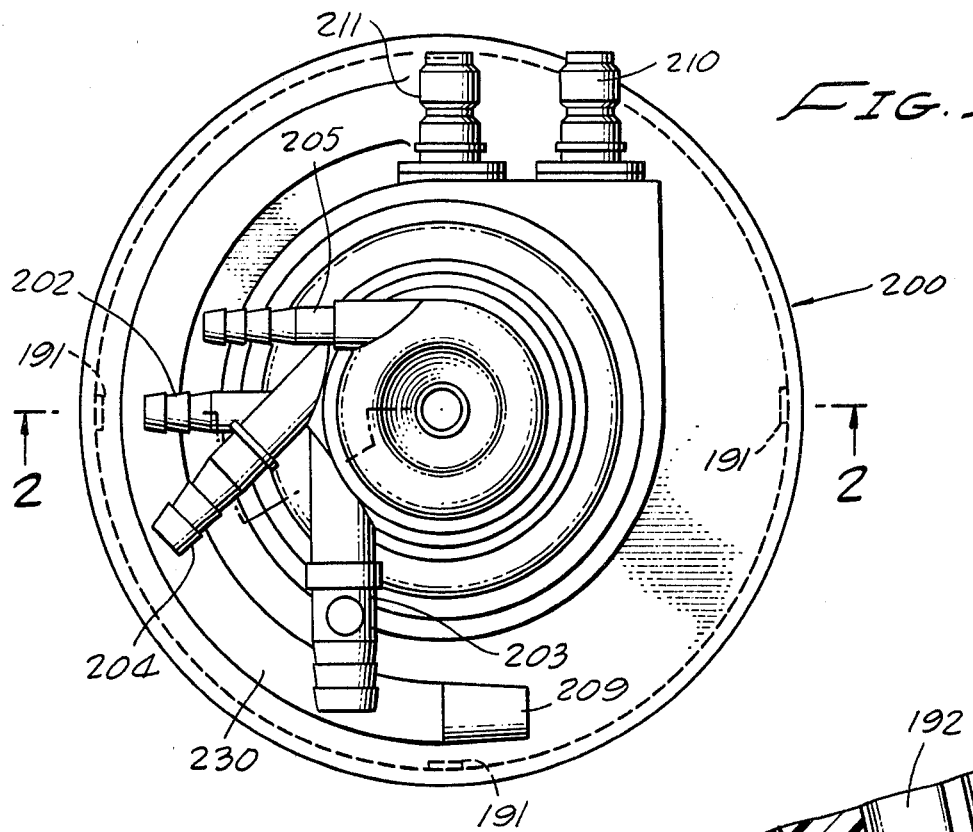
FIG. 1 is a top view of the oxygenator of this invention.
Figure 2:
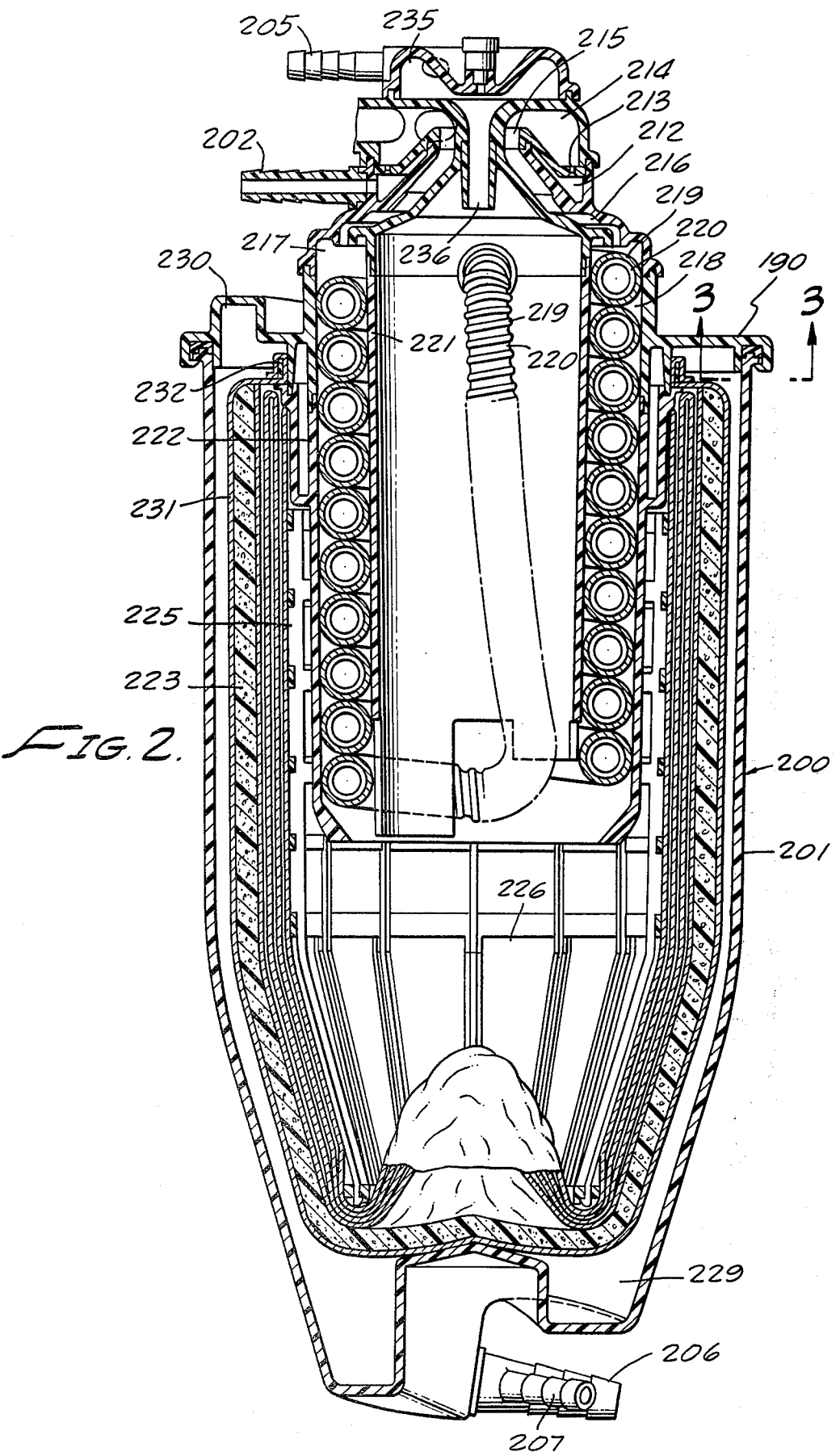
FIG. 2 is a cross-section taken about 2—2 of FIG. 1.

As shown in FIG. 1 the oxygenator 200 of this invention includes an oxygen-containing gas inlet 202 and blood inlets 203 and 204. Inlet 205 is provided for priming as well as for optimal medical administration and, if needed, as a return inlet from the cardiotomy reservoir. A gas vent 209 is provided as are inlet 210 and outlet 211 for heat exchanger fluid. Gas inlet 202, blood inlets 203 and 204, inlet 205, vent 209 and heat exchanger fluid inlet 210 and outlet 211 are preferably located in the cap portion 190, as shown in FIG. 2. This cap portion 190 of the blood oxygenator 200 is rotatably connected to an outer shell portion 201 of the oxygenator 200. Preferably, the outer shell portion 201 of the blood oxygenator includes blood outlets 206 and 207.

Referring now to FIG. 2, the internal construction of the oxygenator 200 is shown in greater detail. As there depicted, gas inlet 202 connects with annular chamber 212 which is bounded on its upper end by diffusion means 213. This diffusion means 213 may be of a suitable pores or perforated apertured member, but preferably is a perforated member.

Blood inlet means 203 and 204 connect with the interior of the annular chamber 214 in a generally tangential manner. Thus, when chamber 214 is filled with blood, flowing in a spiral manner, the oxygen-containing gas is admitted to the device through inlets 202. This gas, such as oxygen or an oxygen-rich mixture, passes through inlet 202 into chamber 212 and through diffusion means 213 into the body of the blood in chamber 214.

Chamber 214 connects with annular chamber 215 and undulating distribution channel 216, the latter being conical in general shape. Channel 216 connects with annular mixing chamber 217 which is provided with heat exchange tube 218 and which contains a descending flow path for the blood. Heat exchange tubing 218 is a convoluted tubing having a large diameter portion 219 and a small diameter portion 220. Thus, although the heat exchange tubing has a large diameter 219 which is essentially the same diameter as the radial distance between the inner wall 221 and outer wall 222 of the mixing chamber, there are a plurality of descending flow paths between the walls of mixing chamber and the wall of tubing 218 formed by the convolution. In addition, since tubing 218 is helically wrapped about inner wall 221, there is a helically descending flow path through the mixing chamber.

At the lower end of chamber 217, outer wall 222 terminates approximately two-thirds of the distance from the top to the bottom of the oxygenator to permit bubbles of blood to come into contact with the defoaming means 223. Thus the elevation of the blood outlets 206 and 207 is lower than the bottom of the tortuous flow path to the mixing chamber. While several defoaming means may be used, e.g., that disclosed in U.S. Pat. No. 3,468,631, it is perferred to form the foaming material from a polyurethane foam having approximately ten to thirty pores per inch. The polyurethane foam is coated with a silicone defoaming agent. Optimally, a spacer 225 may be provided between the defoaming material 223 and wall 222. Spacer 225 may comprise a rib structure which provides open spaces therebetween.

Open spaces 226 are provided in spacer 225 which permits blood to come into contact with defoaming material 223. The lower end of the oxygenator is provided with reservoir 229 where liquid blood is collected.

Figure 4:
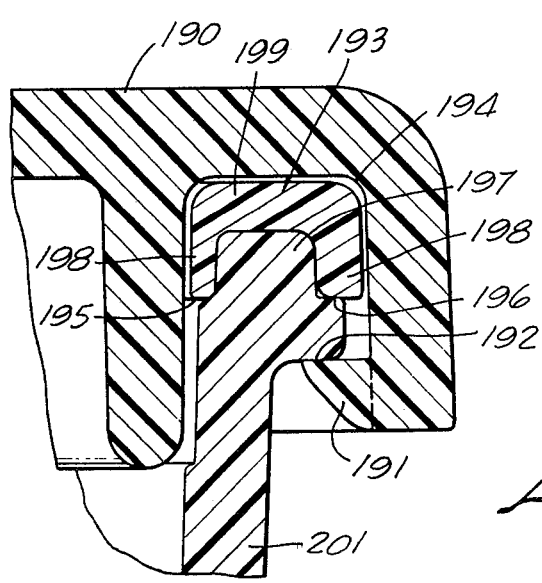
FIG. 4 is a partial cross-sectional view of the oxygenator of this invention.

Annular passage 230 connects with the vent means 209 so that vent gases may be exhausted from the oxygenator. As will be more fully described when FIG. 4 is discussed in greater detail, the rotatable joint between cap portion 190 and outer shell 201 also provides for the venting of gases from the oxygenator 200. A mesh sleeve 231 which may be polyester, polypropeylene, polyethelene, nylon or other suitable fabric is positioned about the defoaming material 223 and is provided with elastic bands 232 to hold it in place. Port 205 connects with chamber 235 which, in turn, connects with conduit 236. Port 205 is used for priming the oxygenator and may also be used for addition of medication to the blood or for blood coming from cardiotomy reservoir.

Figure 3:
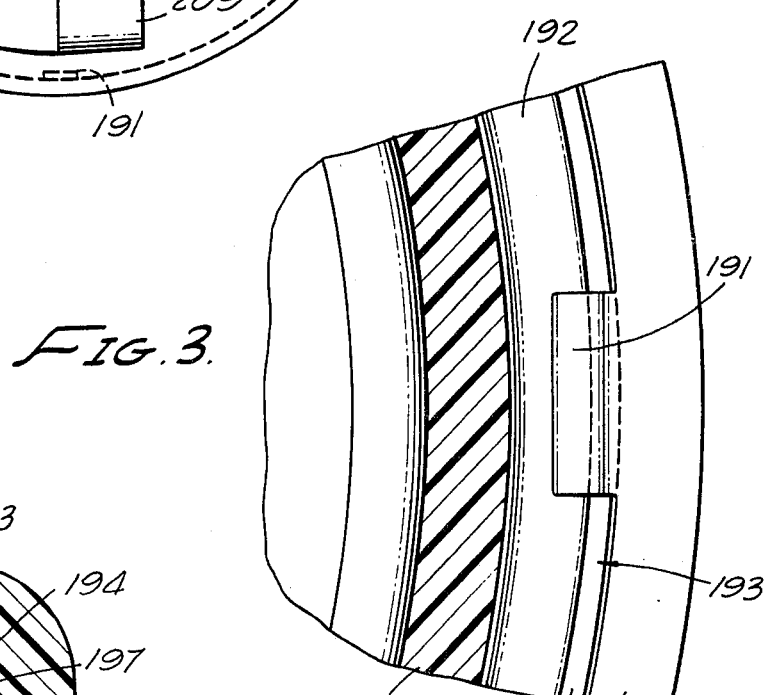
FIG. 3 is a cross-section taken about 3—3 of FIG. 2.

Referring now to FIG. 4, the rotatable joint between the cap portion 190 and the outer shell 201 will be described in detail. The outer periphery of cap portion 190 includes an annular recess portion 194 within which channel-shaped bearing surface 193 may be positioned so as to bear against shoulders 195 and 196 of outer shell 201. Projection 197 of outer shell 201 is in contact both with flange portions 198 and web portion 199 of the channel shaped bearing surface 193. Cap portion 190 further includes tabs 191 which bear upon shoulder 192 of outer shell 201 in order to secure outer shell 201 and cap portion 190 and cause the projection 197 to bear against web portion 199 of channel shaped bearing surface 193. The interrelationship between the tab portion 191 of cap portion 190 and shoulder 192 of shell 201 are shown in greater detail in FIG. 3. Preferably, the cap portion 190 and outer shell portion 201 are formed from a polycarbonate and the channel shaped bearing surface is acetal resin, such as "Delrin" a trademark of E. I. Dupont, which reduces friction at the bearing surface.

The rotatable joint between cap portion 190 and outer shell 201 is preferably located adjacent annular passage 230 which is in venting communication with vent 209 so that vent gases may be exhausted from the oxygenator either through vent means 209 or, secondarily, through the unpressurized rotatable connection between cap portion 190 and outer shell 201. It is preferred that this rotatable connection be between the cap portion 190 and outer shell portion 201, because this selection of the location for a rotatable connection between portions of the oxygenator 200 does not require pressurized fittings in order to prevent potential blood leakage from the device. The ability to rotate cap portion 190 relative to outer shell 201 allows for the operator of the device to ensure that flexible tubing connecting the oxygenator 200 to incoming blood or oxygen-rich gas or outgoing oxygenated blood will not be partially occluded or kinked so as to restrict the effectiveness of the operation of the device. Similarly, the rotatable connection between cap portion 190 and outer shell 201 prevents any partial occlusion with respect to flexible tubing connected to point 205 which may be used for priming the oxygenator 200 as well as for optimal medical administration or a return inlet from a cardiotomy reservoir. Further, the rotation of the outer shell 201 with respect to cap portion 190 allows for the operator of the oxygenator 200 to rotate the outer shell 201 and blood outlets 206 and 207 attached thereto in order to closely monitor the operation of the oxygenator 200 during certain portions of the oxygenator operation including initial setup of the device when it is important to insure that there are no gas bubbles at the blood outlets 206 and 207. It is also often desirable to closely monitor the blood outlets 206 and 207 during the conclusion of the oxygenating procedure when the blood level within the oxygenator is being drawn down near blood outlets 206 and 207 in order to return as much blood as possible to the patient while ensuring that a proper blood level is maintained within the device.

It is to be understood that the present invention is not to be limited to any particular theory of operation. However, in an effort to provide a completed disclosure as possible in the mode of operation of the present invention, the description in which follows is believed to be accurate on the basis of present information.

In operation of the oxygenator 200, oxygen enters through port 202 and passes through a passageway 212 and perforated member 213. The oxygen then mixes with blood entering through ports 203 and 204 and the mixture flows in a spiral direction through chamber 214 in the passageway 215 and then into conical passage 216 which has an undulating cross-section. This undulating cross-section permits secondary flow and the bubbled blood is spread outwardly and down into bubble column 217 where it continues to flow downwardly through two primary flow paths across heat exchanger tubing 218. The oxygenated blood mixture subsequently passes through defoaming means 223 and outward through blood outlets 206 and 207.

What is claimed is:

1. An apparatus for oxygenating blood comprising:
   a housing having an outer shell portion and a cap portion closing the upper end of said outer shell portion, said cap portion having fixedly mounted thereon:
   a blood inlet means;
   an oxygen-containing gas inlet means;
   an excess oxygen and carbon dioxide vent means;
   a wall means suspended from said cap portion and extending in a direction toward the bottom of said outer shell portion and spaced radially inwardly therefrom, said wall means defining therewithin a blood oxygenating chamber with said blood and oxygen-containing gas inlet means communicating therewith;
   said wall means and said outer shell portion defining therebetween a vent chamber in communication with said blood oxygenating chamber;
   said excess oxygen and carbon dioxide vent means communicating with said vent chamber;
   an oxygenated blood outlet means connected to said outer shell portion;
   said cap portion being rotatably joined to said outer shell portion at the upper portion of said vent chamber thereby allowing for cap rotation without possibility of blood loss from the device, and whereby the cap portion and shell portion are relatively rotatable during oxygenation of blood.

2. The apparatus for oxygenating blood claimed in claim 1 wherein the rotatable joint between the cap portion and the outer shell portion is further defined as including a channel-shaped bearing surface including channel and web portions between said cap portion and said outer shell portion.

3. The apparatus for oxygenating blood claimed in claim 2 wherein said rotatable joint is further defined as including a projection of said outer shell portion which bears against said web portion and said flange portions of said channel shaped bearing surface.

4. The apparatus for oxygenating blood claimed in claim 3 wherein said rotatable joint further includes a plurality of tab members annularly spaced about the exterior of said cap portion for engaging a shoulder of said outer shell portion.

5. The apparatus as claimed in any one of claims 2, 3, or 1 wherein the rotatable joint provides a secondary vent path for gas from the oxygenator.

* * * * *